United States Patent [19]

Horodysky et al.

[11] Patent Number: 5,336,420
[45] Date of Patent: * Aug. 9, 1994

[54] ANTIOXIDANTS FOR FUNCTIONAL FLUIDS

[75] Inventors: Andrew G. Horodysky, Cherry Hill, N.J.; Shih-Ying Hsu, Morrisville, Pa.; Andrew Jeng, Paulsboro; Leslie R. Rudnick, Lawrenceville, both of N.J.

[73] Assignee: Mobil Oil Corporation, Fairfax, Va.

[*] Notice: The portion of the term of this patent subsequent to Mar. 16, 2010 has been disclaimed.

[21] Appl. No.: 989,861

[22] Filed: Dec. 14, 1992

Related U.S. Application Data

[63] Continuation-in-part of Ser. No. 697,039, May 8, 1991, Pat. No. 5,194,167.

[51] Int. Cl.$^5$ ............................................. C10M 135/36
[52] U.S. Cl. ..................... 252/34; 252/34.7; 252/47.5; 252/402; 548/127; 548/128; 548/129; 548/130; 548/134; 548/135; 548/136
[58] Field of Search ............... 252/34, 34.7, 47.5, 252/402; 548/127, 128, 130, 129, 134, 135, 136

[56] References Cited

U.S. PATENT DOCUMENTS

| | | | |
|---|---|---|---|
| 4,410,703 | 10/1983 | Okorodudu | 548/142 |
| 4,584,114 | 4/1986 | Gemmill et al. | 252/47.5 |
| 4,661,273 | 4/1987 | Frangatos et al. | 252/47 |
| 4,678,592 | 7/1987 | Toukan | 252/25 |
| 5,194,167 | 3/1993 | Hsu et al. | 252/34 |

Primary Examiner—Jacqueline V. Howard
Attorney, Agent, or Firm—Alexander J. McKillop; Malcolm D. Keen; Jessica M. Sinnott

[57] ABSTRACT

An aromatic functional fluid, specifically a monoalkylated tetradecyl diphenyl oxide synthetic lubricant, contains a polymer-supported reaction product of an organic quaternary ammonium salt, derived from a mercapto-heterocycle and a quaternary ammonium salt. To produce the polymer-supported organic quaternary ammonium salt, the salt is reacted with a dicarboxylic acid or anhydride, specifically 2-dodecen-1-ylsuccinic anhydride. An arylamine antioxidant, such as alkylated phenyl naphthylamine, can be added to the polymer supported organic quaternary ammonium salt-treated functional fluid to impart extra antioxidant and stability properties.

27 Claims, No Drawings

ANTIOXIDANTS FOR FUNCTIONAL FLUIDS

CROSS REFERENCE TO RELATED APPLICATIONS

This application is a continuation-in-part application of U.S. patent application Ser. No. 07/697,039 filed on May 8, 1991, now U.S. Pat. No. 5,194,167, which is entitled "Quaternary Ammonium Salts of Mercaptothiadiazoles and Related Heterocyclic Derivatives as Antioxidant and Antiwear Additives". The foregoing application is incorporated herein by reference in its entirety.

FIELD OF THE INVENTION

This application is directed to a functional fluid containing a reaction product of a quaternary ammonium salt and a mercapto-heterocycle and polymer supported derivatives thereof. More specifically, the application is directed to an aromatic functional fluid containing the polymer supported reaction product which exhibits unexpected antioxidant properties.

BACKGROUND OF THE INVENTION

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation leads to a loss of lubrication properties, and in especially severe cases this may cause complete breakdown of the device being lubricated. Many additives have been tried, however, many of them are only marginally effective except at high concentrations. Improved antioxidants are clearly needed.

Antioxidants or oxidation inhibitors are used to minimize the effect of oil deterioration that occur when hot oil is contacted with air. The degree and rate of oxidation will depend on temperature, air and oil flow rates and, of particular importance, on the presence of metals that may catalytically promote oxidation. Antioxidants generally function by prevention of peroxide chain reaction and/or metal catalyst deactivation. They prevent the formation of acid sludges, darkening of the oil and increases in viscosity due to the formation of polymeric materials.

The use of thiadiazole derivatives, such as 2,5-dimercapto-1,2,4-thiadiazole, for their antioxidant, anticorrosion and metal passivating properties when incorporated into oleaginous compositions is well known as disclosed in U.S. Pat. Nos. 4,661,273, 4,678,592 and 4,584,114. U.S. Pat. No. 4,410,703 discloses the use of thiadiazoles substituted with certain other moieties such as the organophosphorous moiety.

Traditional quaternary ammonium salts consist of a) a tetra-alkylated amine cation, and b) an inorganic counter-anion such as halide, perchlorate or hexafluorophosphate. These quaternary salts have been widely used in industrial and household applications as cleaning detergents. Little or no attention has been given to them for use as lubricant additives due to their ionic nature which can make them incompatible with and insoluble in organic fluids. However, these problems have been solved in a recent discovery reported in U.S. patent application Ser. No. 07/697,039 to Horodysky et al. There, it is described that selected quaternary ammonium salts converted into organic quaternary ammonium salts are soluble in organic fluids. These organic quaternary ammonium salts demonstrated solubility in both mineral base stocks and ester-based synthetic lubricants and exhibited good antioxidant and antiwear activities.

SUMMARY OF THE INVENTION

This invention is directed to an improvement on Ser. No. 07/697,039 now U.S Pat. No. 5,194,167. It was discovered that a reaction product of a quaternary ammonium salt, a mercaptothiadiazole and a dicarboxylic acid or anhydride exhibited superior antioxidant properties in aromatic fluids, particularly when combined with an arylamine antioxidant.

The quaternary ammonium compound disclosed is different from those prior art ionic compounds containing acidic protons such as a mixture of carboxylic acids and amines which are not desirable in lubricant compositions because they may act as pro-oxidants or oxidation accelerators. The organic quaternary ammonium salt disclosed herein contains no undesirable acidic protons. Its use as an antioxidant additive in an aromatic functional fluid demonstrated unexpected antioxidant benefits.

DESCRIPTION OF PREFERRED EMBODIMENTS

A mercapto-heterocycle is reacted with a quaternary ammonium halide in the presence of an alkanol and an alkali metal hydroxide. The resulting product can be reacted with a dicarboxylic acid or anhydride to produce a polymer-supported reaction product.

The organic ammonium salt antioxidant is easily prepared at ambient temperature in almost quantitative yields.

The quaternary ammonium salt is represented by the following structural formula:

$$R_1R_2R_3R_4N^+X^-$$

where $R_1$, $R_2$, $R_3$ and $R_4$ of the tetra-substituted ammonium ion are the same or different; hydrocarbon groups containing about 1 to 40 carbon atoms, preferably 1 to 18 carbon atoms which can be alkyl or aryl or a combination thereof and X is an anion, a negatively charged acid radical. The hydrocarbon groups can contain at least one heteroatom which can be a sulfur atom, nitrogen atom and/or an oxygen atom. The anion can be an element selected from Group VIIB of the Periodic Table of the Elements, such as fluorine, chlorine, bromine or iodine, it can also be a sulfate, nitrate or any other common anion.

Although an ammonium cation is typical, there are other suitable types of organic cations such as N-alkyl pyridinium halide, sulfonium salts, or triphenylmethyl salts. Representative examples of suitable quaternary ammonium salts include tricaprylylmethylammonium chloride (ALIQUAT 336), octadecyldimethylbenzyl ammonium chloride, tetraethylammonium chloride, tetrapentyl ammonium chloride, dicoco dimethyl ammonium chloride (VARIQUAT K300), dialkyl $C_{12}$-$C_{18}$ dimethyl ammonium chloride (ANDOGEN 432), ditallow dimethyl ammonium chloride (ANDOGEN 470) and hexamethonium chloride.

The organic salt can be used in an unalkylated form or an alkylated (or polymer-supported) form.

The quaternary ammonium salts disclosed are made from mercapto-heterocyclic compounds containing from 1 to 3 mercapto groups. All or essentially all of the mercapto groups are converted to form the described salt derivative.

A suitable mercapto-heterocycle is a mercapto-thiadiazole. Some suitable examples include but are not limited to 3,4-dimercapto-1,2,5-thiadiazole, 3,5-dimercapto-1,2,4-thiadiazole, 4,5-dimercapto,1,2,5-thiadiazole, 4,5-dimercaptobenzo 1,2,3-thiadiazole, 4,7-dimercaptobenzo 1,2,3-thiadiazole, 4,6-dimercaptobenzo 1,2,3-thiadiazole, 5,6-dimercaptobenzo 1,2,3-thiadiazole, 5,7-dimercaptobenzo 1,2,3-thiadiazole, 6,7-dimercaptobenzo 1,2,3-thiadiazole, 4,5-dimercaptobenzo 2,1,3-thiadiazole, 4,6-dimercaptobenzo 2,1,3-thiadiazole, 5,6-dimercaptobenzo 2,1,3-thiadiazole, 5,7-dimercaptobenzo 2,1,3-thiadiazole, 6,7-dimercaptobenzo 2,1,3-thiadiazole and 2,5-dimercapto-1,3,4-thiadiazole. Other examples of mercapto-heterocycles include mercaptothiazoles, such as 2-mercaptobenzothiazole, mercapto-diazacyclohexenes and mercaptothiazolines.

The organic cations as noted above are not limited to quaternary ammonium salts but can include other organic cations as noted hereinabove.

The following mechanism illustrates the reaction when the anion is chlorine, and the mercapto-heterocycle is 2-mercaptobenzothiazole (FIG. 1) and 2,5-dimercapto-1,3,4-thiadiazole (FIG. 2):

Figure 1

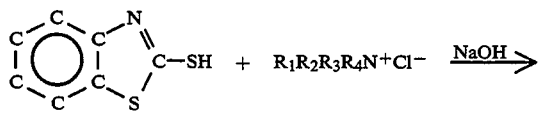

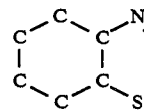

Figure 2

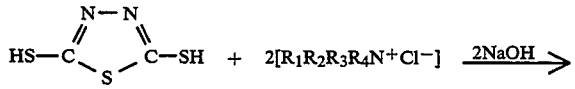

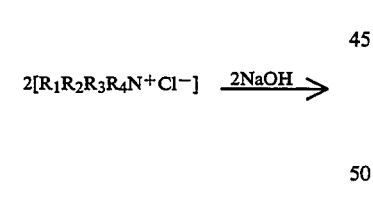

-continued

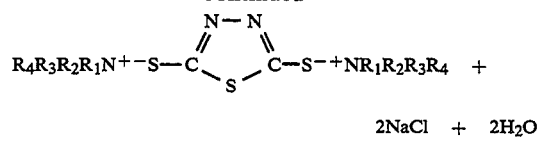

where $R_1$, $R_2$, $R_3$ and $R_4$ of the tetra-substituted ammonium ion are described above.

The organo quaternary ammonium salt can be reacted with a dicarboxylic acid or anhydride to produce an alkylated (polymer-supported) product. A representative esample of a suitable dicarboxylic anhydride is a hydrocarbon-substituted succinic anhydride which can be represented by the structural formula:

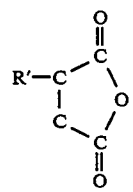

where R′ is a hydrocarbon group containing from about 1 to about 40 carbon atoms, preferably $C_{12}$ to $C_{40}$ carbon atoms. The hydrocarbon group is, preferably, an aliphatic alkyl or alkenyl group. The hydrocarbon group can be straight chain or branched.

The hydrocarbon-substituted succinic anhydride can be derived from a condensation reaction between an olefin and maleic anhydride. Suitable olefine include ethylene, propylene, butylene, isobutylene, pentylene, heptylene, decylene, dodecylene, eicosene, higher olefinic hydrocarbons as well as polymers and copolymers made from any of the foregoing olefins. The olefin can also contain cyclic hydrocarbon groups such as phenyl, naphthyl or alicycle. The hydrocarbon group can contain at least one heteroatom which is a nitrogen atom, sulfur atom or oxygen atom. Specific examples of hydrocarbon-substituted succinic anhydrides include 2-dodecen-1-ylsuccinic anhydride, polyisobutenyl or isobutenylsuccinic anhydride or polypropenylsuccinic anhydride. Dicarboxylic acids are also expected to work, a specific dicarboxylic acid is exemplified by dodecenyl succinic acid.

The following FIG. 3 illustrates the reaction mechanism for producing the alkylated/(polymer supported) form of the quaternary ammonium salt of the invention when a substituted succinic anhydride is reacted with the reaction product of FIG. 2.

Figure 3

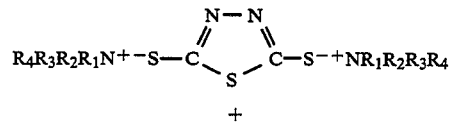

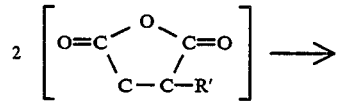

Figure 3

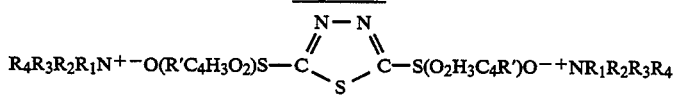

where R′, $R_1$, $R_2$, $R_3$ and $R_4$ are as described above.

Although the above structures are believed to be present in the products, other reaction products may form. We do not want to be bound by the products shown.

Conditions for the above reactions may vary widely depending upon specific reactants, the presence or absence of a solvent and the like. Any suitable set of reaction conditions known to the art may be used. A solvent or diluent can be added to facilitate the course of reaction. Hydrocarbon solvents such as an alcohol; i.e. methanol, ethanol or isopropanol; aromatic hydrocarbon, i.e. toluene or xylenes, can be used. Stoichiometric or equimolar ratios of reactants are used as well as more than equimolar or less than equimolar amounts. For example, when two moles of the dicarboxylic are reacted with one equivalent amount of the salt, a dialkylated salt, as shown in FIG. 3, is produced. When one mole of the dicarboxylic is reacted with one equivalent amount of the salt a monoalkylated salt is produced.

The mercapto-heterocycle is reacted in the presence of an alkali metal hydroxide at ambient to slightly elevated temperatures ranging from about 0° C. to about 50° C., more specifically from about 15° C. to about 30° C. under ambient pressure. An alkali metal salt precipitate forms during the reaction which can be removed by filtration. Reaction times range from about 0.5 hours to 50 hours, more specifically about 1 to 10 hours. The solvent can be removed by vacuum or atmospheric distillation. Reaction conditions are not, however, viewed as critical.

The polymer-supported organic quaternary ammonium salt provides exceptional antioxidant activity with corrosion inhibiting and metal passivating properties when utilized in aromatic functional fluids.

It was discovered that the additive embodied herein utilized in an aromatic functional fluid, particularly, an alkyl aromatic functional fluid exhibited unexpected antioxidant properties. The aromatic functional fluid, more specifically, an aromatic lubricant fluid, even more specifically, a lubricant oil, can be manufactured synthetically or can be of mineral oil origin such as a refined crude oil made by solvent refining, or a thermally or catalytically cracked oil, alkylated aromatic hydrocarbon or an oil made by hybrid processing which is a combination of solvent refining and hydrotreating. Specific examples of aromatic functional fluids include alkylated diphenyl oxides, e.g. a monoalkylated tetradecyl diphenyl oxide, alkylated diphenyl methanes, alkylated diphenyl sulfides, alkylated-thiophenes, benzothiophenes, dibenzothiophenes, phenoxathins, phenothiazines and alkylated naphthalenes. The organic quaternary ammonium compound is combined with the functional fluid in an amount which imparts significant antioxidant characteristics to the fluid. Concentrations of about 0.001 to about 10 wt. % based on the total weight of the composition can be used. Preferably, the concentration is from 0.1 to about 10 wt. %, even more preferably from about 0.5 to about 3 wt. %.

The term "functional fluid" is used for purposes of defining a group of fluids which have lubricative properties. Such fluids include lubricative concentrates which can be utilized in water-based emulsions or they can be lubricant oil basestocks. Applications for these fluids include use as gear oils, e.g. automotive spiral-bevel and worm-gear axle oils which operate under extreme pressures, load and temperature conditions, hypoid gear oils operating under both high speed, low-torque and low-speed, high torque conditions. Other uses include industrial applications which include circulation oils and steam turbine oils, gas turbine oils, for both heavy-duty gas turbines and aircraft gas turbines, way lubricants, mist oils and machine tool lubricants. Engine oils are also contemplated such as diesel engine oils, i.e., oils used in marine diesel engines, locomotives, power plants and high speed automotive diesel engines, gasoline burning engines, such as crankcase oils and compressor oils. Still other uses include automotive fluids such as automatic transmission fluids, power steering fluids and power brake fluids.

The basestock can be a combination of functional fluids, i.e. the aromatic functional fluids which demonstrate unexpected antioxidant properties, or a blend thereof, as well as a non-aromatic fluid, i.e., a lubricative mineral or synthetic oil. In such a case, a ratio of aromatic functional fluid to non aromatic fluid of 6:1 to 1:6, specifically, from 1:4 to 4:1 is contemplated. Suitable synthetic fluids include polyisobutylenes, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by butyl-substituted bis(p-phenoxy phenyl) ether and phenoxy phenylethers.

It is also contemplated that the functional fluid composition can be employed in the form of a grease in which the lubricating oil is used in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount sufficient to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for foaming grease can be used in preparing grease in accordance with the present invention.

It is a particularly important finding that an aromatic functional fluid composition of this invention which comprises an organic quaternary ammonium compound exhibits even better antioxidant properties when combined with an arylamine antioxidant. Specific examples of arylamine antioxidants include: N-dodecylphenyl-1-naphthylamine; alkyl-substituted diphenylamines, such as p,p'-di-octyldiphenylamine, iso-alkyl diphenylamines, such as p,p'-di-t-octyldiphenylamine and branched p,p'-dinonyldiphenylamine, aromatic and alkyl aromatic-substituted aromatic amines, such as styrenated diphenylamines, N-phenyl-1-naphthylamine, N-t-octylphenyl-1-naphthylamine and α-phenylalkyldiphenylamines, i.e. α-phenylethyldiphenylamine, phenylenediamines and alkyl-substituted phenylenediamines. Aromatic-containing heterocyclic amines are also contemplated such as 2,2,4-trimethylquinoline and 1,2-dihydro-2,2,4-trimethylquinoline. Mixtures of any of the foregoing aromatic amines are also contemplated.

The arylamine antioxidant is blended into the quaternary ammonium salt-treated fluid in an amount ranging from about 0.1 to 5.0 wt. %, specifically from about 0.25 to 1.5 wt. %, by conventional blending techniques. The proportion of quaternary ammonium salt to arylamine antioxidant can range from about 1 to 10 to about 10 to 1, more specifically, about 1:5 to 5:1 based on the entire weight of the additive composition.

It is to be understood, however, that the compositions contemplated herein can also contain other materials. For example, corrosion inhibitors, extreme pressure agents, low temperature property modifiers and the like can be used as exemplified respectively by metallic phenates or sulfonates, sulfurized isobutylenes, acrylate polymers and the like. These materials do not detract from the value of the compositions of this invention, rather the materials serve to impart their customary properties to the particular compositions in which they are incorporated.

The following examples describe specific embodiments of the invention.

EXAMPLE 1

This example illustrates an embodiment of the invention in which a 2-dodecen-1-ylsuccinic anhydride polymer support is reacted with the organic quaternary ammonium salt of 2,5-dimercapto-1,3,4-thiadiazole in a molar ratio of 2:1.

To a solution of 2,5-dimercapto-1,3,4-thiadiazole (30 g, 0.2 mol) in methanol (200 ml) was added sodium hydroxide (16 g, 0.4 mole) at ambient temperature, 25° C. The solution was stirred for 30 min. and Aliquat 336 (tricaprylylmethylammonium chloride, Henkel Corp.) (162 g, 0.4 mol) was slowly added. Sodium chloride precipitated out during the addition. When the addition was complete, stirring was continued at ambient temperature for one hour. The mixture was filtered to remove the solid and the solvent was evaporated to afford a greenish oil which was used without purification. 2-Dodecen-1-ylsuccinic anhydride (106 g, 0.4 mol) was then added and further reacted with or without toluene as a solvent. The solution was filtered and the solvent was removed by vacuum distillation to obtain the final product which was a brownish oil.

EXAMPLE 2

This example illustrates an embodiment of the invention in which a 2-dodecen-1-ylsuccinic anhydride is reacted with the organic quaternary ammonium salt of 2,5-dimercapto-1,3,4-thiadiazole in a mole ratio of 1:1.

To a solution of 2,5-dimercapto-1,3,4-thiadiazole (30 g, 0.2 mol) in methanol or isopropanol (200 ml) was added sodium hydroxide (16 g, 0.4 mol) at ambient temperature, about 25° C. The solution was stirred for 30 min. and Aliquat 336 (tricaprylylmethylammonium chloride, Henkel Corp.) (162 g, 0.4 mol) was slowly added. Sodium chloride precipitated out during the addition. When the addition was complete, stirring was continued at ambient temperature for one hour. The mixture was filtered and the solvent was evaporated to afford a greenish oil which was used without further purification. 2-Dodecen-1-ylsuccinic anhydride (53 g, 0.2 mol) was then added and further reacted with or without toluene as a solvent. The solution was filtered and the solvent was removed by vacuum distillation to obtain the final product which was a brownish oil.

The following examples demonstrate the procedure for making the treated lubricants.

EXAMPLE 3

A blended sample of 99 weight percent of an aromatic lubricating fluid of predominantly monoalkylated tetradecyl diphenyl oxide and one weight percent of a quaternary ammonium salt, made in accordance with the procedure of Example 1 was prepared by mixing at room temperature, about 25° C.

EXAMPLE 4

A blended sample of 99 weight percent of an aromatic lubricating fluid of predominantly monoalkylated tetradecyl diphenyl oxide and 1 weight percent of an arylamine antioxidant (octylated phenylnaphthylamine) was prepared by mixing at room temperature, about 25° C.

EXAMPLE 5

A blended sample of monoalkylated tetradecyl diphenyl oxide and 1 weight percent of a hindered phenolic antioxidant (Ethyl Corp.'s Ethyl 702) was prepared in accordance with Example 4.

EVALUATION OF PRODUCTS

The organic ammonium salt antioxidant blended with an alkylated diphenyl oxide synthetic lubricant, described in Example 3, was evaluated for antioxidant performance in the Catalytic Oxidation Test at 325° F. for 40 hours (Table 1). The oxidation-inhibiting characteristics of the inorganic ammonium salt was compared with a commercially available hindered phenol antioxidant and an arylamine antioxidant blended in the same base stock, as described in Examples 4 and 5.

CATALYTIC OXIDATION TEST

In the catalytic oxidation test, the lubricant is subjected to a stream of air which is bubbled through the lubricant at the rate of five liters per hour at elevated temperatures for a specified time (Table 1, 325° F. for 40 hours). Present in the composition are samples of metals commonly used in engine construction, namely, iron, copper, aluminum, and lead. See U. S. Pat. No. 3,682,980, incorporated herein by reference for further details.

TABLE 1

Catalytic Oxidation Test (325° F., 40 hrs

| Item | Change in Acid Number Δ TAN | Change in Viscosity % Δ KV | Lead Loss (%) | Sludge |
|---|---|---|---|---|
| Base oil (Alkylated Diphenyl Oxide Lubricant) | 12.43 | 101 | 57.8 | Moderate |
| Commercial Hindered Phenol Antioxidant (Ethyl Corp, Ethyl 702) in above base oil (1 wt. %) | 0.44 | 4 | 1.7 | Nil |
| Commercial Arylamine Antioxidant (octylated phenylnaphthylamine) in above base oil (1 wt. %) | 0.31 | 6.84 | 3.79 | Light |
| Example 1 in above base oil (1 wt. %) | 0.78 | 0.48 | 0.47 | Light |

It is clear from the data presented in Table 1 that an organic quaternary ammonium salt antioxidant prepared as described herein exhibited excellent antioxidant activity when compared to commercially available arylamine and hindered phenol antioxidants in an alkylated diphenyl oxide lubricant.

The following Examples illustrate the production of a fully formulated compressor oil treated with an antioxidant made as described herein.

EXAMPLE 6

The quaternary ammonium salt of Example 1 was blended into a synthetic compressor oil package. The compressor oil was a hydroprocessed basestock containing commercial antiwear and defoamant additives.

EXAMPLE 7

The procedure of example 6 was followed with the exception that 1.75 wt. % of the quaternary ammonium salt was blended into the oil.

EXAMPLE 8

The quaternary ammonium salt of Example 1 in an amount of 0.5 wt. %, and an arylamine antioxidant (an octylated phenylnaphthylamine) in an amount of 0.5 wt. % were blended into the synthetic compressor oil package, as described in Example 6.

EXAMPLE 9

The procedure of example 8 was followed with the exceptions that 1 wt. % of the quaternary ammonium salt and 0.75 wt. % of the arylamine antioxidant were blended into the oil.

The following Tables 2 and 3 facilitate an evaluation of the antioxidant performance of the treated compressor oils of Examples 6-9. Tables 2 and 3 show that the addition of a minor amount of an arylamine antioxidant to a fully formulated synthetic compressor oil improved the antioxidant properties of the blended product over the same compressor oil made with just the quaternary ammonium salt, and no arylamine. Tables 2 and 3 report a comparison of the antioxidant properties of compressor oil containing 1 wt. % and 1.75 wt. % of the organic quaternary ammonium salt with the antioxidant properties of a compressor oil containing 0.5 wt. % of an arylamine and 0.5 wt. % of the organic quaternary ammonium salt as well as the antioxidant properties of the oil containing 0.75 wt. % quaternary ammonium salt and 1.00 wt. % organic quaternary ammonium salt.

TABLE 2

Treated Synthetic Compressor Oil Catalytic Oxidation Test F., 40 hrs.

| Run | Arylamine Antioxidant (wt. %) | Example 1 (wt. %) | % ΔKV | ΔTAN | % Pb loss | sludge |
|---|---|---|---|---|---|---|
| 1 | — | 1 | 105 | 9.09 | 39.4 | light |
| 2 | 0.5 | 0.5 | 5.85 | −2.8 | 0.39 | trace |

TABLE 3

Treated Synthetic Compressor Oil Catalytic Oxidation Test 375° F., 24 hrs.

| Run | Arylamine Antioxidant (wt. %) | Example 1 (wt. %) | % Δ KV | ΔTAN | % Pb loss | sludge |
|---|---|---|---|---|---|---|
| 1 | — | 1 | 136 | 7.85 | 31.17 | light |
| 2 | — | 1.75 | 107 | 9.87 | 31.2 | moderate |
| 3 | 0.5 | 0.5 | 2.3 | 0.44 | 0.59 | light |
| 4 | 0.75 | 1.0 | 11.88 | 3.11 | 10.6 | light |

OXIDATION STABILITY TEST

The compounds of this invention also display good stability properties as indicated by the results of a Rotary Bomb Oxidation Test. The Rotary Bomb Oxidation Test was followed in accordance with ASTM Method D 2272. In the test, the sample to be evaluated, water and a copper coil, which was catalytically active, were placed in a glass container. The container was placed in a bomb with a pressure meter. Oxygen (90 psi, 6.2 bars) was charged to the bomb and the bomb was heated to and maintained at a constant temperature of 150° C. and rotated axially at 100 rpm at an angle of 30 deg. The oxygen pressure was recorded. The temperature was maintained until there was a pressure drop of 25.4 psig (1.75 bars) from the maximum autogenous pressure. The results reported in Tables 4 and 5 were the time (in minutes) after which the indicated pressure drop took place. A long period of time corresponds with an effective stabilizer. Table 4 reports the results of the test using an alkylated diphenyl oxide lubricant prepared as described in Examples 3, 4 and 5. Table 5 reports the results of the test using a fully formulated compressor oil prepared as described in Examples 6, 7, 8 and 9. Table 5 shows that the addition of an arylamine antioxidant along with the organic quaternary ammonium salt increases the stability of the oil.

TABLE 4

ROTATING BOMB OXIDATION TEST (ASTM D 2272) Alkylated Diphenyl Oxide Lubricant

| | Time (minutes) |
|---|---|
| Alkylated Diphenyl Oxide Lubricant | 175 |
| Commercial Phenol Antioxidant (Ethyl Corp. Ethyl 702) in above base oil (1 wt. %) | 320 |
| Commercial Aryl Amine Antioxidant (octylated phenylnaphthylamine) in above base oil (1 wt. %) | 1200 |
| Example 1 in above base oil (1 wt. %) | 44 |

TABLE 5

Treated Synthetic Compressor Oil
Rotating Bomb Oxidation Test (ASTM D 2272)

| Run | Arylamine Antioxidant (wt. %) | Example 1 (wt. %) | Time for Oxidation (minutes) |
|---|---|---|---|
| 1 | — | 1 | 120 |
| 2 | — | 1.75 | 131 |
| 3 | 0.5 | 0.5 | 390 |
| 4 | 0.75 | 1.00 | 197 |

What is claimed is:

1. An improved functional fluid composition comprising a major proportion of an aromatic functional fluid and a minor proportion of a reaction product of a mercaptoheterocyclic compound selected from the group consisting of mercaptobenzothiazoles and dimercaptothiadiazoles and a quaternary ammonium salt at temperatures ranging from about 0° C. to about 50° C.

2. The composition of claim 1 in which the reaction product is further reacted with a dicarboxylic acid or anhydride in an equimolar, less than equimolar or more than equimolar amount.

3. The composition of claim 2 in which the dicarboxylic anhydride is a hydrocarbon-substituted succinic anhydride.

4. The composition of claim 3 in which the hydrocarbon-substituted succinic anhydride has the following structural formula:

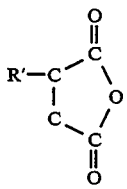

where R' is a hydrocarbon group containing from about 1 to about 40 carbon atoms.

5. The composition of claim 4 in which the hydrocarbon-substituted succinic anhydride is 2-dodecen-1-ylsuccinic anhydride.

6. The composition of claim 1 in which the mercaptoheterocyclic compound is 2-mercaptobenzothiazole.

7. The composition of claim 1 in which the mercaptoheterocyclic compound is 2,5-dimercapto-1,3,4-thiadiazole.

8. The composition of claim 2 in which the reactants are 2,5-dimercapto-1,3,4-thiadiazole, tricaprylylmethylammonium halide, and 2-dodecen-1-ylsuccinic anhydride.

9. The composition of claim 1 in which the functional fluid is an alkylated aromatic oil.

10. The composition of claim 1 in which the functional fluid composition contains from about 0.1 to about 5.0 wt % of the reaction product based on the total weight of the composition.

11. The composition of claim 2 in which the functional fluid is an alkylated diphenyl methane, alkylated diphenyl sulfide, alkylated-thiophene, benzothiophene, dibenzothiophene, phenoxathin, phenothiazine, alklyated naphthalene or combination thereof.

12. The composition of claim 8 in which the aromatic functional fluid is an alkylated diphenyl oxide.

13. The composition of claim 12 in which the alkylated diphenyl oxide is a monoalkylated tetradecyl diphenyl oxide.

14. The composition of claim 1 which further comprises an arylamine antioxidant.

15. The composition of claim 14 in which the arylamine antioxidant is an alkyl aromatic substituted-naphthylamine, an alkyl-substituted diphenylamine, an iso-alkyl diphenylamine, an aromatic or alkyl aromatic-substituted aromatic amine, a phenylalkyldiphenylamine, a styrenated diphenylamine, a phenylenediamine, an alkyl-substituted phenylenediamine or an aromatic-containing heterocyclic amine or a mixture of any of the foregoing aromatic amines.

16. The composition of claim 15 in which the arylamine antioxidant is N-dodecylphenyl-1-naphthylamine, p,p'-di-octyldiphenylamine, branched p,p'-di-t-octyldiphenylamine, branched p,p'-dinonyldiphenylamine, N-phenyl-1-naphthylamine, N-t-octylphenyl-1-naphthylamine, α-phenylethyldiphenylamine, 2,2,4-trimethylquinoline or 1,2-dihydro-2,2,4-trimethylquinoline.

17. The composition of claim 1 which further comprises a non-aromatic functional fluid which is a mineral oil or synthetic oil.

18. A process of preparing a functional fluid composition comprising blending a major amount of an aromatic functional fluid with a minor antioxidant amount of a polymer-supported reaction product of an organic quaternary ammonium salt, derived from a mercaptoheterocyclic compound selected from the group consisting of mercaptobenzothiazoles and dimercaptothiadiazoles and a quaternary ammonium salt at temperatures ranging from about 0° C. to about 50° C.

19. The process of claim 18 in which the polymer support is derived from a dicarboxylic acid or anhydride.

20. The process of claim 19 in which the dicarboxylic anhydride is 2-dodecen-1-ylsuccinic anhydride.

21. The process of claim 20 in which the reactants are 2,5-dimercapto-1,3,4-thiadiazole, tricaprylylmethylammonium halide, and 2-dodecen-1-ylsuccinic anhydride.

22. The process of claim 18 in which the functional fluid is an alkylated aromatic oil.

23. The process of claim 22 in which the alkylated aromatic oil is an alkylated diphenyl oxide.

24. The process of claim 23 in which the alkylated diphenyl oxide is a monoalkylated tetradecyl diphenyl oxide.

25. The process of claim 18 in which the functional fluid composition further comprises an arylamine antioxidant.

26. The process of claim 25 in which the arylamine antioxidant is an alkyl aromatic substituted-naphthylamine, an alkyl-substituted diphenylamine, an iso-alkyl diphenylamine, an aromatic or alkyl aromatic-substituted aromatic amine, a phenylalkyldiphenylamine, a phenylenediamine, an alkyl-substituted phenylenediamine or an aromatic-containing heterocyclic amine or a mixture of any of the foregoing aromatic amines.

27. The process of claim 26 in which the arylamine antioxidant is N-dodecylphenyl-1-naphthylamine, p,p'-di-octyldiphenylamine, branched p,p'-di-t-octyldiphenylamine, branched p,p'-dinonyldiphenylamine, N-phenyl-1-naphthylamine, N-t-octylphenyl-1-naphthylamine, α-phenylethyldiphenylamine, 2,2,4-trimethylquinoline or 1,2-dihydro-2,2,4-trimethylquinoline.

* * * * *